United States Patent [19]

Kotick et al.

[11] 4,443,605
[45] Apr. 17, 1984

[54] 7β-ARYLALKYL-6α, 7 α-OXYMETHYLENE-3-METHOXY OR 3-HYDROXY-4, 5α-EPOXY-17 METHYL OR 17-CYCLOALKYL-METHYL MORPHINANS

[75] Inventors: Michael P. Kotick; David L. Leland, both of Elkhart, Ind.

[73] Assignee: Miles Laboratories, Inc., Elkhart, Ind.

[21] Appl. No.: 403,464

[22] Filed: Jul. 30, 1982

[51] Int. Cl.³ .................. C07D 489/02; A61K 31/485
[52] U.S. Cl. ........................................ 546/39; 424/260; 546/44
[58] Field of Search ............................ 546/39; 424/260

[56] References Cited

U.S. PATENT DOCUMENTS 3,432,486  5/1969  Minato ........................... 546/44 X
4,275,205  1/1981  Kotick et al. ........................ 546/44

OTHER PUBLICATIONS

Kotick, et al., J. Med. Chem. 24(12), p. 1445–1450 (1981).
Leland, et al., J. Org. Chem., 48(11), pp. 1813–1819 (1983).
J. Med. Chem., 26 (7), pp. 1050–1056 (1983), Kotick, et al.
Leland, et al., J. Med. Chem., vol. 24, No. 6, pp. 717–721 (06/81).

*Primary Examiner*—Donald G. Daus
*Assistant Examiner*—Diana Rivers
*Attorney, Agent, or Firm*—Jerome L. Jeffers

[57] ABSTRACT

Disclosed are 7β-arylalkyl substituted morphinan compounds characterized by the formula:

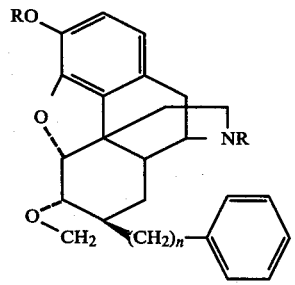

In the above formula, R is H or methyl, $R_1$ is methyl, cyclopropylmethyl or cyclobutylmethyl and n is 2 to 5.

20 Claims, No Drawings

7β-ARYLALKYL-6α, 7 α-OXYMETHYLENE-3-METHOXY OR 3-HYDROXY-4, 5α-EPOXY-17 METHYL OR 17-CYCLOALKYL-METHYL MORPHINANS

BACKGROUND OF THE INVENTION

Morphine is a well-known narcotic analgesic having the structural formula:

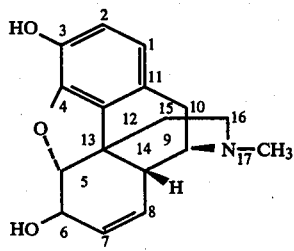

The compounds of this invention are structurally related to morphine and are named according to the morphinan system of nomenclature using the morphinan nucleus as shown below:

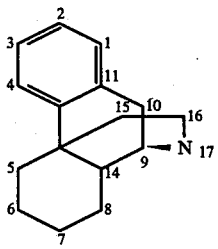

The numbering and the stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for the morphine nucleus unless otherwise indicated.

In U.S. Pat. No. 4,275,205, there is disclosed 7,7-ditosyloxymethyl-4,5α-epoxy-3-methoxy-17-methyl-morphinan-6β-ols of the formula:

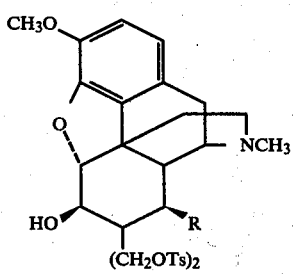

where R is H, $CH_3$ or $CH_2CH_3$. These compounds are precursors for certain 7,7-dimethyl-morphinans having analgesic activity or a combination of analgesic and narcotic antagonist activity.

SUMMARY OF THE INVENTION

The present invention involves 7β-arylalkyl-6α,7α-oxymethylene-3-methoxy or 3-hydroxy-4,5α-epoxy-17-methyl or 17-cycloalkylmethyl-morphinans characterized by the formula:

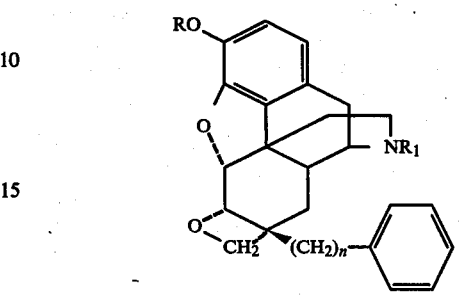

In the above formula, R is H or methyl, $R_1$ is methyl, cyclopropylmethyl or cyclobutylmethyl and n is 2 to 5. These compounds are useful as strong analgesics.

DESCRIPTION OF THE INVENTION

The present invention demonstrates that 2 isomeric morphinan compounds have vastly different analgesic activities. Those compounds in which the large $C_7$ substituent is in the down or α position and the $C_6$ substituent is in the up or β position, are inactive whereas those compounds in which the groups at the $C_6$ and $C_7$ positions have been inverted are potent antinociceptive agents. Greater than a 3,000 fold difference in activity has been demonstrated between these isomers. Changing the length of the methylene bridge between the terminal aryl group and the $C_7$ tertiary carbon in the active isomer also results in changes in the compound's activity.

The inactive 7-α isomeric series is synthesized as illustrated in scheme I. Referring to scheme I, ring closure of 7,7-ditosyloxymethyl-4,5α-epoxy-3-methoxy-17-methyl-morphinan-6β-ol (2) prepared as described in U.S. Pat. No. 4,275,205, is accomplished by treatment with dilute aqueous sodium hydroxide in refluxing 2-butanone to form the 6β,7β-oxymethylene derivative (3). Displacement of the 7α-tosyloxy group by acetate gives (4) which is saponified to the 7α-hydroxymethyl compound (5). Oxidation to the 7α-formyl compound (6) is carried out using dimethyl sulfoxide-trifluoroacetic anhydride as the oxidizing agent. Wittig condensation with the ylide derived from cinnamyltriphenylphosphonium chloride gives the 7α-substituted compound (7). Hydrogenation in the presence of HCl gives both the desired 7α-phenylbutyl compound (8) and the oxymethylene cleaved compound (9). Compound (8) was inactive at 10 mg/kg in the acetic acid induced writhing assay described infra. This is contrasted with the 7β-phenylbutyl6α,7α-oxymethylene derivative (17e, scheme II) which has an $ED_{50}$ in the same assay of 0.003 mg/kg.

The synthesis of the highly potent 7β-arylalkyl series starts with the same ditosyloxy compound (2). The 6β-hydroxy group in (2) is inverted to a 6α-hydroxy group by an oxidation reduction sequence. Oxidation of the 6β-ol in (2) to the 6-oxo compound (10) is carried out using dimethylsulfoxide-trifluoroacetic anhydride in methylene chloride solution at about −60° C. Stereoselective reduction to the 6α-ol (11) is effected by reduction of (10) with sodium borohydride in an ethanol-chloroform mixture at ice-bath temperature. Ring closure to the 6α,7α-oxymethylene-7β-tosyloxymethyl compound (12) is carried out using 3 equivalents of a 1 N sodium hydroxide solution in aqueous dioxane at about 70° C. for 1 hour. The 7β-tosyloxymethyl group is displaced from (12) with sodium acetate in dimethylformamide solution to give (13) which is hydrolyzed with methanolic sodium hydroxide to the 7β-hydroxymethyl compound (14). Oxidation of (14) to the key intermediate 7β-formyl compound (15) is accomplished using dimethylsulfoxide-trifluoroacetic anhydride as described above.

The 7β-arylalkyl group is extended from the 7β-formyl compound (15) [scheme III] by use of the Wittig reaction. Various triphenylphosphonium arylalkyl ylides for condensation with (15) were prepared using either sodium hydride-dimethylsulfoxide or phenyl lithium as the base. A side product with phenyl lithium was an isomeric mixture of the tertiary alcohols (18). Independent preparation of (18) by reaction of (15) with phenyl lithium gave this same mixture of side products which could be separated into pure isomers by chromatography.

The unsaturated intermediates (16) were catalytically hydrogenated to saturated compounds (17) under neutral conditions. This reaction at times proceeded with difficulty, but repurification of the starting material by chromatography and/or the addition of more catalyst overcame this reluctance to reduction.

The 3-methoxy compounds (17) were converted to the corresponding 3-hydroxy compounds in a 2-step process. Treatment of (17) with refluxing 48% hydrobromic acid for 10 to 15 minutes opened the acid labile oxetane ring as well as cleaving the 3-methoxy group to give (19). Mild base treatment of bromomethylene compound (19) at 60°–70° C. for 90 minutes in aqueous dioxane resulted in reclosure of the oxetane ring and the desired 3-hydroxy-6α,7α-oxetane-7β-arylalkyl compounds (20) could be isolated in moderate overall yields.

Reaction of (17) with cyanogen bromide proceeded smoothly. Since the 6α,7α-oxymethylene ring is sensitive to acidic reagents, hydrolysis of cyano compound (21) to nor compound (22) was carried out using potassium hydroxide in refluxing dioxane for a period of 5 to 7 days. The isolated nor compounds were not further characterized but were converted to N-cycloalkylmethyl compounds (23 P,B) by reaction with the appropriate cycloalkylmethyl bromide in DMF solution in the presence of sodium bicarbonate at 100° C. until the reaction was complete as indicated by thin layer chromatography.

The isolated N-cycloalkylmethyl compounds (23 P,B) were converted to the 3-hydroxy analogs (24 P,B) by the 2-step refluxing HBr-dilute base treatment as indicated above for compound (21).

SCHEME I

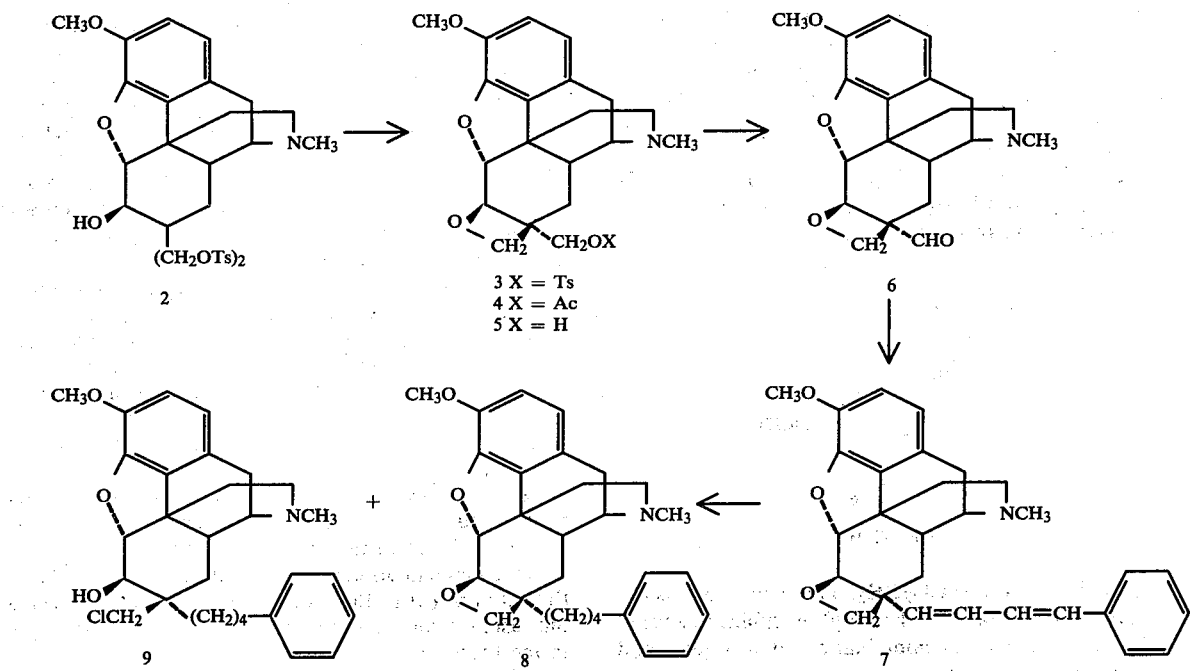

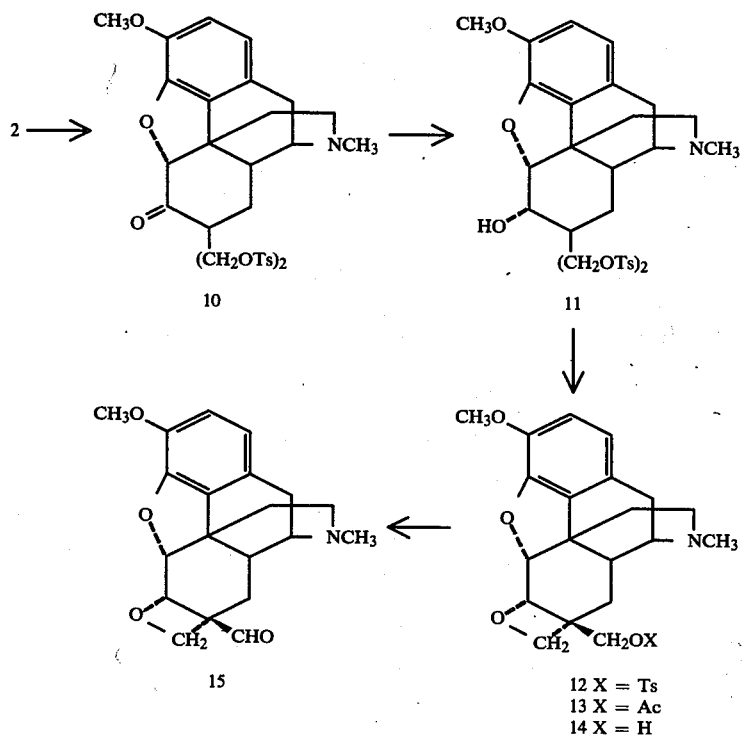
SCHEME II
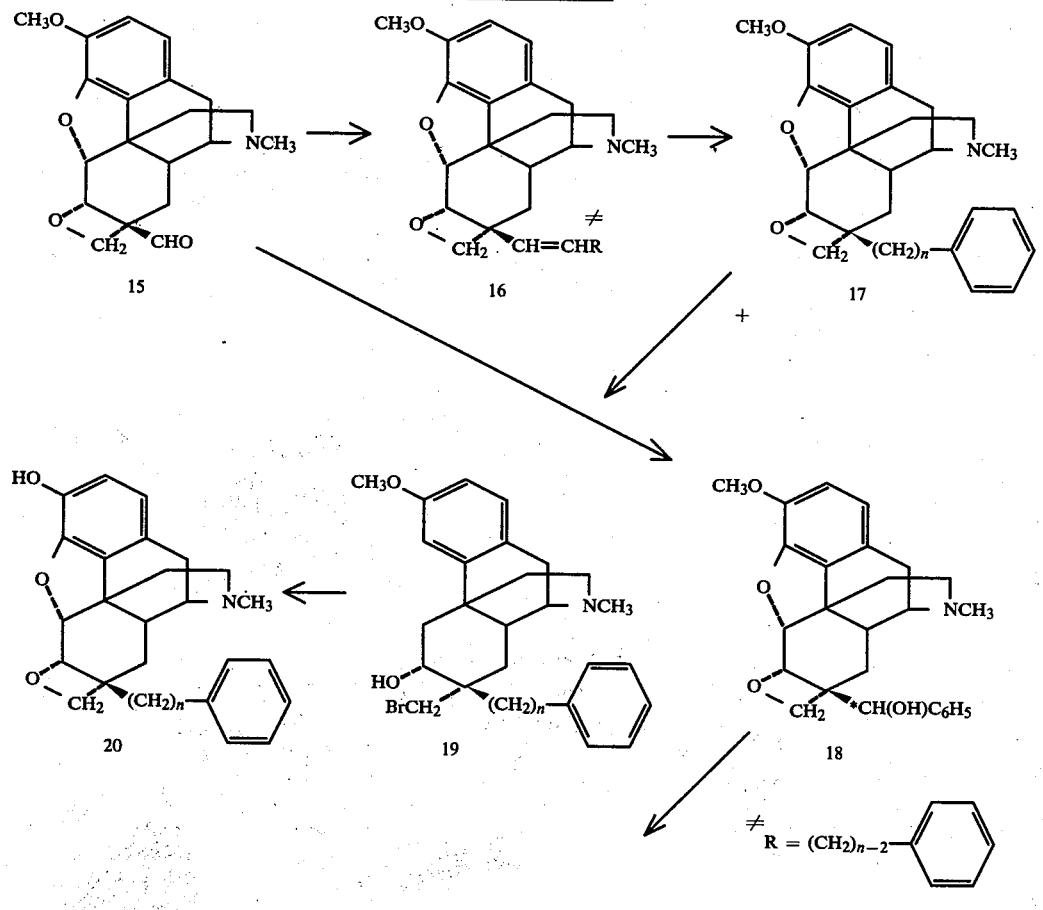
SCHEME III

-continued
SCHEME III

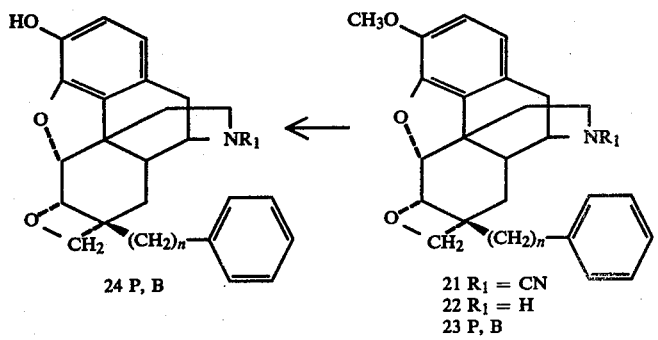

P = cyclopropylmethyl (CPM)
B = cyclobutylmethyl (CBM)

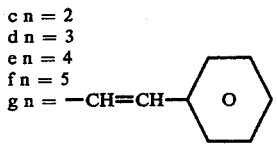

c n = 2
d n = 3
e n = 4
f n = 5
g n = —CH=CH—⟨O⟩

The method of preparing the compounds of the present invention and their utility as strong analgesic agents are further illustrated by the following examples where the term "processing in the usual manner" means that the combined organic phases were washed with dilute NH$_4$OH, dried (MgSO$_4$), filtered and evaporated at 40°–45° C. bath temperature. The residue was further dried under high vacuum at 50°–60° C. bath temperature. Column chromatography was carried out over Silica Gel 60 G (E. Merck) using CHCl$_3$-MeOH mixtures containing 0.25 to 1% v/v concentrated NH$_4$OH. NMR spectra were determined in CDCl$_3$ unless otherwise noted.

EXAMPLE I

Preparation of Inactive C$_7$-α Substituted Morphinans

A.
4,5α-Epoxy-3-methoxy-17-methyl-7α-tosyloxymethyl-6β,7β-(oxymethylene)-morphinan (3)

A solution of crude 2 (16.3 g, 24 mmole) in 2-butanone (200 mL) containing 1 N NaOH (25 mL) was refluxed for 2 hrs. After concentration, the residue was partitioned between dilute NH$_4$OH and CHCl$_3$. Processing of the CHCl$_3$ extracts in the usual fashion gave 11.0 g (95%) of a glass which contained ~90% of 3 as indicated by TLC. This glass was used without further purification in the succeeding reaction. Material prepared in another reaction was purified by chromatography to give a 73% yield of homogeneous 3; NMR δ 7.87–7.27 (m, 4H, tosyl aromatic); 6.73 (m, 2H, H1 and H2); 4.47 (d, 2H, J=5 Hz); 4.30 (q, 2H); 3.90 (s, 3H, CH$_3$O—); 2.48 (s, 6H, CH$_3$N—, tosyl CH$_3$—).

B.
7α-Acetoxymethyl-4,5α-epoxy-3-methoxy-17-methyl-6β,7β-(oxymethylene)-morphinan (4)

A mixture of 3 (2.5 g, 5 mmole) and NaOAc (0.6 g, 7.5 mmole) in DMF (75 mL) was heated in an oil bath at 100° C. while under argon for 18 hrs. The mixture was evaporated in high vacuum and the residue partitioned between dilute NH$_4$OH and PhMe. Evaporation of the organic phase gave 1.87 g (97%) of 4 as a glass which contained traces of 5 as indicated by TLC; NMR δ 1.83 (s, 3H, CH$_3$COO—).

C.
4,5α-Epoxy-7α-hydroxymethyl-3-methoxy-17-methyl-6β,7β-(oxymethylene)-morphinan (5)

A solution of 4 (3.25 g, 8.4 mmole) in MeOH (50 mL) was stirred with NaOMe (0.68 g, 12.6 mmole) for 30 min. The solution was evaporated to dryness and the residue partitioned between H$_2$O and CHCl$_3$. Processing in the usual fashion gave 2.65 g of a foam which was chromatographed to yield 1.90 g (66%) of 5 as a foam. This foam was converted to the d-tartrate salt which gave crystals of 5.d-tartrate, mp sinters 170° C., melts 198°–218° C. with foaming, from aqueous EtOH.

Anal. Calcd. for C$_{20}$H$_{25}$NO$_4$·C$_4$H$_6$O$_6$: C, 58.41; H, 6.33; N, 2.64. Found: C, 58.80; H, 6.22; N, 2.82.

D.
4,5α-Epoxy-7α-formyl-3-methoxy-17-methyl-6β,7β-(oxymethylene)-morphinan (6)

A solution of trifluoroacetic anhydride (1.97 mL, 14.0 mmole) in CH$_2$Cl$_2$ (10 mL) was added dropwise to a solution of DMSO (1.32 mL, 18.6 mmole) in CH$_2$Cl$_2$ (15 mL) under argon at −60° C. After stirring of this mixture for 10 min., a solution of 5 (3.2 g, 9.3 mmole) in CH$_2$Cl$_2$ (50 mL) was added slowly dropwise at −60° C. The mixture was stirred for 90 min. at dry iceacetone bath temperature and TEA (2 mL) added dropwise. The solution was warmed to room temperature and washed with several portions of dilute NH$_4$OH. Processing gave 3.0 g of a foam which was chromatographed. First eluted was 2.3 g (72%) of 6 which was obtained as a foam; NMR δ 9.55 (s, 1H, 7α-CHO). Continued elution gave 0.9 g (28%) of recovered starting material 5.

E.
4,5α-Epoxy-3-methoxy-17-methyl-7α-(4-phenyl-1,3-butadienyl)-6β,7β-(oxymethylene)-morphinan (7)

A suspension of 50% NaH (641 mg, 13.3 mmole) in mineral oil was washed with hexane under an atmosphere of argon and then DMSO (10 mL) added. The mixture was heated at 60°–70° C. until the evolution of H$_2$ ceased (~30 min.), then it was cooled to 25° C. and a solution of cinnamyltriphenylphosphonium chloride (5.54 g, 13.3 mmole) in DMSO (50 mL) added dropwise. The deep red solution was stirred 10 min. and 6 (2.28 g, 6.7 mmole) in DMSO (50 mL) added rapidly dropwise. The mixture was stirred for 30 min. at ambient temperature and then heated at 65°–70° C. for 30 min. The mixture was cooled, diluted with water and the resulting solution adjusted to pH ∼3 with concentrated HCl. After extraction with 3 portions of PhMe, the solution was made basic with NH$_4$OH and again extracted with PhMe. The organic extracts of the basic solution were evaporated to give 4.24 of a red syrup which consisted of a major and minor alkaloidal product. Chromatography gave 1.02 g (35%) of the pure major product 7 as a foam. Continued elution gave an additional 0.74 g of a double bond isomeric mixture of 7 for an overall yield of 60%. Crystallization of the initially eluted pure isomer from EtOH gave an analytical sample of 7, mp sinters 76° C., melts 84°–86° C.; mass spectrum m/e 441 (M+, 100); 412 (49).

Anal. Calcd. for C$_{29}$H$_{31}$NO$_3$: C, 78.88; H, 7.08; N, 3.17. Found: C, 78.55; H, 7.17; N, 2.98.

F.
4,5α-Epoxy-3-methoxy-17-methyl-7α-(4-phenylbutyl)-6β,7β-(oxymethylene)-morphinan (8) and 7β-chloromethyl-4,5α-epoxy-3-methoxy-17-methyl-7α-(4-phenylbutyl)-morphinan-6β-ol (9)

A solution of 7 (1.0 g) in 95% EtOH was made slightly acidic with HCl and then hydrogenated over 10% Pd/C (0.4 g) at an initial pressure of 50 psi for 3 hrs. The catalyst was removed by filtration, the filtrate evaporated and the residue dissolved in H$_2$O. After the addition of NH$_4$OH, the mixture was extracted with CHCl$_3$. Processing in the usual manner gave 1.1 g of a foam which was chromatographed. Eluted first from the column was 509 mg (47%) of 9 which was obtained as a foam on evaporation; NMR δ 7.23 (s, 5H, Ph-); 6.73 (s, 2H, H1 and H2); 4.52 (d, 1H, H5, J=7 Hz); mass spectrum m/e 483 (38); 481 (100). Continued elution followed by evaporation of homogeneous fractions gave 293 mg (29%) of crystalline 8 which was recrystallized from EtOAc to give shiny white crystals, mp 144°–145° C.; NMR δ 7.5-7.0 (m, 5H, Ph-); 6.72 (m, 2H, H1 and H2); broad s at 4.63 and 4.48 for 1H each and 4.3 for 2H; mass spectrum m/e 445 (M+, 100); 414 (30); 388 (26).

Anal. Calcd. for C$_{29}$H$_{35}$NO$_3$: C, 78.17; H, 7.92; N, 3.14. Found: C, 78.02; H, 8.00; N, 3.02.

EXAMPLE II
Preparation of Active C$_7$-β Substituted Morphinans

A.
7,7-Bis(tosyloxymethyl)-4,5α-epoxy-3-methoxy-17-methyl-morphinan-6-one (10)

A solution of crude 2 (66.6 g, 99.4 mmole) in CH$_2$Cl$_2$ (250 mL) was added dropwise under argon to a mixture prepared from DMSO (14.2 mL, 200 mmole) in CH$_2$Cl$_2$ (100 mL) and TFAA (21.2 mL, 150 mmole) in CH$_2$Cl$_2$ (70 mL) as reported above for 6. The mixture was stirred in the dry ice acetone bath for 90 min. TEA (40 mL) was added and the mixture then allowed to warm to room temperature. The solution was evaporated, the residue dissolved in CHCl$_3$ and washed 3 times with dilute NH$_4$OH. Evaporation of the dried organic phase gave a foam which crystallized from 95% ethanol to give 53.8 g (81%) of 10 as white crystals, mp 150°–153° C. Recrystallization from 95% ethanol gave analytically pure 10, mp 155°–156° C.; NMR δ 7.2-7.9 (m, 8H, tosyl H's); 7.70 (s, 2H, H1 and H2); 4.47 (s, H5).

Anal. Calcd. for C$_{23}$H$_{37}$NO$_9$S$_2$: C, 61.15; H, 5.58; N, 2.10. Found: C, 61.18; H, 5.58; N, 1.85.

B.
7,7-Bis(tosyloxymethyl)-4,5α-epoxy-3-methoxy-17-methyl-morphinan-6α-ol (11)

A solution of 10 (20.0 g, 30 mmole) in a mixture of 95% EtOH (200 mL) and CHCl$_3$ (100 mL) was cooled in an ice bath and NaBH$_4$ (3.4 g, 90 mmole) added portionwise over 10 min. The mixture was stirred for 90 min. in the cold, excess HOAc added to destroy the hydride and the solution evaporated. The residue was partitioned between CHCl$_3$ and dilute NH$_4$OH and further processed in the usual fashion. Evaporation gave a quantitative yield of 11 as a foam which contained traces of 6β-ol 2 and other impurities; NMR δ 4.41 (d, 1H, H5, J=5.5 Hz). This material was converted to 12 without further purification.

C.
4,5α-Epoxy-3-methoxy-17-methyl-7β-tosyloxymethyl-6β,7β-(oxymethylene)-morphinan (12)

Compound 11 (20.0 g, 29.9 mmole) in dioxane (600 mL) containing 1N NaOH (90 mL) was stirred in a preheated oil bath at 65°–70° C. for 1 hr. The mixture was evaporated to a small volume and the residue processed with CHCl$_3$ in the usual fashion. Evaporation of the CHCl$_3$ gave 13.8 g (93%) of 12 as a foam which contained trace impurities. Material purified by chromatography had the following NMR δ 7.93-7.26 (q, tosyl H's); 6.68 (m, H1 and H2); 4.60 (pair of doublets, 2H, 7α-CH$_2$O—, J=8 Hz and 24 Hz), 4.26 (d, 1H, H5, J5,6=5.5 Hz), 4.02 (s, 2H, —CH$_2$OTs), 3.90 (CH$_3$O—), 3.42 (d, 1H, H6).

D.
7β-Acetoxymethyl-4,5α-epoxy-3-methoxy-17-methyl-6α,7α-(oxymethylene)-morphinan (13)

A mixture of 12 (13.8 g, 27.7 mmole) and NaOAc (3.45 g, 41.6 mmole) in DMF (325 mL) was heated for 18 hrs. at 80° C. under an argon atmosphere. The DMF was removed under high vacuum, the residue dissolved in CHCl$_3$ and washed with dilute NH$_4$OH. Further processing gave 12.3 g of 13 as a crystalline solid. Another similar reaction gave a 93% yield of 13 which was crystallized and recrystallized from EtOH to give an analytical sample of 13, mp 149°–150° C.

Anal. Calcd. for C$_{22}$H$_{27}$NO$_5$: C, 68.55; H, 7.06; N, 3.63. Found: C, 68.42; H, 7.38; N, 3.50.

E.
4,5α-Epoxy-7β-hydroxymethyl-3-methoxy-17-methyl-6α,7α-(oxymethylene)-morphinan (14)

To a solution of 13 (12.3 g; 32 mmole) in MeOH (200 mL) was added 1 N NaOH (25 mL) and the mixture stirred for 1 hr. The solution was evaporated and the residue partitioned between CHCl$_3$ and dilute NH$_4$OH. Further processing gave 12.6 g of a foam which was predominantly 14. Crystallization from EtOAc-Et$_2$O gave 8.4 g (77%) of 14, mp 179°–181° C. Recrystallization from EtOH gave an analytical sample of 14, mp 180°–181.5° C.; NMR δ 3.63 (s, 2H, —CH$_2$OH); mass spectrum, m/e 343 (M+, 100), 272 (77).

Anal. Calcd. for C$_{20}$H$_{25}$NO$_4$: C, 69.95; H, 7.34; N, 4.08. Found: C, 69.67; H, 7.62; N, 4.22.

F. 4,5α-Epoxy-7β-formyl-3-methoxy-17-methyl-6α,7α-(oxymethylene)-morphinan (15)

A solution of 14 (17.2 g, 50 mmole) in $CH_2Cl_2$ (225 mL) was oxidized using DMSO (100 mmole) and TFAA (75 mmole) in $CH_2Cl_2$ (90 mL) for 90 min. as described above. After the addition of TEA (20 mL) and processing in the usual fashion, 15.2 g (89%) of 15 was obtained as a foam: NMR δ 9.10 (s, CHO); 6.67 (m, aromatic); 5.25 1 (d, 1H, —CHO—, J=7 Hz); 4.53 (m, 2H, —CHO— and H5); 3.87 ($CH_3O$—), 3.45 (d, H6, J=5.5 Hz).

G. 7β-Arylalkyl-4,5α-epoxy-3-methoxy-17-methyl-6α,7α-(oxymethylene)-morphinan (17)

These compounds were prepared by reaction of 7β-formyl compound 15 with the appropriate triphenylphosphonium ylide. The ylide was generated from the triphenylphosphonium salt by use of either sodium hydride-dimethyl sulfoxide (Method A) or phenyl lithium (Method B) as the base. These general methods are outlined infra followed by the details for the preparation of the specific compounds.

Method A. A suspension of 50% NaH (0.66 g, 13.8 mmole) in mineral oil was washed 3 times with hexane while under an argon atmosphere. DMSO (10 mL) was added and the mixture heated at 60°-70° C. until the evolution of $H_2$ ceased (ca. 30 min.). The mixture was cooled at 25° C. and the appropriate phosphonium salt (13.8 mmole) in DMSO (50 mL) added dropwise. After 10 min., 15 (5.0 g, 12.5 mmole) in DMSO (50 mL) was added rapidly dropwise. Stirring was continued for 30 min. at room temperature followed by heating of the mixture at 65°-70° C. for 30 min. The cooled mixture was processed as described below.

Method B. To a suspension of the phosphonium salt (23 mmole) in $Et_2O$ (200 mL), under argon at room temperature, was added phenyl lithium (23 mmole, 1.9 M solution in 7:3 $C_6H_6$-$Et_2O$) and the mixture stirred for 1-2 hrs. A solution of 15 (4.0 g, 10 mmole) in THF (100 mL) was added to the dark solution and stirring continued for 2 hrs. The reaction was quenched by the addition of $H_2O$, concentrated $NH_4OH$ added and the intermediate 16 extracted with $CHCl_3$. Further processing was conducted as described infra.

Compound 16c was prepared by Method A from 15 and benzyltriphenylphosphonium chloride. Upon completion of the reaction with the phosphonium ylide, the mixture was poured into $H_2O$. The pH of this solution was adjusted to ca. 2 and the aqueous solution extracted several times with PhMe to remove $(C_6H_5)_3PO$. The aqueous phase was made basic with 50% NaOH and 16c extracted into $CHCl_3$. A mixture of the 2 isomers of 16c was obtained in nearly quantitative yield. Hydrogenation of 16c was carried out in aqueous EtOH at 50 psi, with several changes of catalyst (10% Pd/C) until the reduction was complete as indicated by TLC. Workup gave 17c, as a foam, in 74% yield based on 15. This was converted to the d-tartrate salt which was crystallized and recrystallized from EtOH to give pure 17c.d-tartrate, mp 192°-197° C.

Anal Calcd. for $C_{27}H_{31}NO_3.C_4H_6O_6$: C, 65.59; H, 6.57; N, 2.47. Found: C, 65.90; H, 6.51; N, 2.60.

The intermediate ylide for compound 16d was prepared by Method B from phenylethyltriphenylphosphonium bromide. Reaction as described above followed by selective extraction then chromatography gave a 44% yield of 16d. Hydrogenation of 16d for several days gave 17d as a glass in 68% yield from 16d. The d-tartrate salt, mp 191°-192° C., was obtained as crystals from MeOH-EtOAc.

Anal. Calcd. for $C_{28}H_{33}NO_3.C_4H_6O_6$: C, 66.08; H, 6.76; N, 2.41. Found: C, 66.21; H, 6.65; N, 2.27.

Compound 16g, as a mixture of double bond isomers, was prepared as described above for Method A from 50% NaH dispersion (2.92 g, 60.9 mmole), DMSO (75 mL) and cinnamyltriphenyl-phosphonium chloride (25.3 g, 60.9 mmole) in DMSO (200 mL) with addition of the aldehyde 15 (18.9 g, 55.3 mmole) in DMSO (350 mL). Further processing followed by extraction of the basic solution with $CHCl_3$ gave 22.7 g of a foam which contained 2 major alkaloidal spots in addition to traces of $Ph_3PO$. The mixture was chromatographed. Partial resolution of the alkaloidal material provided fractions for further characterization. The faster migrating component crystallized from EtOAc to give grey crystals, mp 188°-189° C.; NMR δ 7.25 (m, 5H, phenyl), 6.70-5.56 (m, 6H, H1, H2 and —CH=CH—CH=CH—), 4.86 (q, 2H, 7α-$CH_2O$—, J=7 and 26 Hz), 4.28 (2, 1H, H5, J=5 Hz), 3.87 ($CH_3O$—), 3.52 (d, 1H, H6); mass spectrum, m/e, 441 (M+,59), 412 (58), 91 (100).

Anal. Calcd. for $C_{29}H_{31}NO_3$: C, 78.88; H, 7.08; N, 3.17. Found: C, 78.60; H, 7.36; N, 3.46.

The slower migrating fraction had the following NMR: δ 7.30 (2, 5H, phenyl), 6.68 (m, 2H, H1 and H2), 6.53-5.36 (m, 4H, —CH=CH—CH=CH—), 4.85 (q, 2H, 7α-$CH_2O$—, J=7 and 22 Hz), 4.47 (d, 1H, H5, J=4.5 Hz), 3.90 ($CH_3O$— and H6).

Hydrogenation of 16g in 95% EtOH (250 mL) containing 10% Pd/C (2.5 g), at an initial pressure of 50 psi and 50° C., was carried out for 24 hrs. The catalyst was removed and the filtrate evporated to dryness. The residue was redissolved in 95% EtOH (200 mL) and $H_2O$ (50 mL), fresh 10% Pd/C (2.5 g) added and the mixture hydrogenated at 50 psi and 50° C. for 3 days. Workup gave 9.5 g (82%) of 16e as a foam which contained trace impurities. Material prepared in another reaction was purified by chromatography; NMR δ 7.23 (m, 5H, phenyl), 6.67 (m, 2H, H1 and H2), 4.58 (q, 2H, 7α-$CH_2O$—, J=7 and 15 Hz), 4.15 (d, 1H, H5, J=5 Hz), 3.87 ($CH_3O$—), 3.38 (d, 1H, H6), 2.42 ($CH_3N$—). Conversion of pure 16e to the d-tartrate salt gave material which was recrystallized from EtOH to give shiny white crystals of 16e.d-tartrate, mp 119°-121° C.

Anal. Calcd. for $C_{29}H_{35}NO_3.C_4H_6O_6$: C, 66.54; H, 6.94; N, 2.35. Found: C, 66.27; H, 7.16; N, 2.57.

Compound 16f was prepared by Method A and obtained as a glass in 36% yield after chromatography. Hydrogenation gave 17f as a glass in 66% yield. Conversion to the d-tartrate salt, followed by crystallization from EtOH, gave an analytical sample of 17f.d-tartrate, mp 130°-136° C.

Anal. Calcd. for $C_{30}H_{37}NO_3.C_4H_6O_6$: C, 66.98; H, 7.10; N, 2.30. Found: C, 67.16; H, 6.94; N, 2.48.

H. 4,5α-Epoxy-7β-(α-hydroxybenzyl)-3-methoxy-17-methyl-6α,7α-(oxymethylene)-morphinan (18)

A solution of 15 (1.72 g, 5.0 mmol) in PhMe (100 mL) under argon was treated dropwise with phenyl lithium (10 mmol). After stirring for 30 min., ice and $H_2O$ were added and the organic phase processed in the usual fashion to give 2.08 g (99%) of 19 as a foam. Chromatography allowed resolution of 2 isomers. The faster migrating isomer crystallized from EtOAc-Et₂O to give 19, mp 222°-223° C.

Anal. Calcd. for C₂₆H₂₉NO₄: C, 74.44; H, 6.97; N, 3.34. Found: C, 74.69; H, 7.05; N, 3.30.

The slower migrating isomer, 19, was crystallized from EtOAc to give needles, mp 237°-240° C. Found: C, 74.30; H, 7.01; N, 3.30.

I.
7β-Arylalkyl-4,5α-epoxy-3-hydroxy-17-methyl-6α,7α-(oxymethylene)-morphinan (20)

A mixture of 17 and 48% HBr (1 g in 10-20 mL) was refluxed in a preheated oil bath for 15 min. The cooled solution was diluted with H₂O, made basic with NH₄OH, and the 6α-hydroxy-7β-bromomethyl intermediate 19 extracted with CHCl₃ or EtOAc. After processing of the organic phase and evaporation, the residue was dissolved in dioxane (30 mL) and 1 N NaOH (10 mL) added. The mixture was heated at 60°-70° C. for 90 min., then evaporated to dryness. The residue was dissolved in H₂O and the pH adjusted to ca. 8 with HOAc. Extraction with CHCl₃ was followed by chromatography. Compound 20c was obtained as a foam in 40% yield. The hemi d-tartrate, mp 200°-208° C., crystallized as the hemi solvate from EtOH.

Anal. Calcd. for C₂₆H₂₉NO₃.0.5 C₄H₆O₆.0.5 C₂H₆O: C, 69.44; H, 7.03; N, 2.79. Found: 69.69; H, 7.15; N, 2.96.

In the same manner, 20d was obtained in 64% yield and the d-tartrate salt, mp 234°-236° C., crystallized from aqueous EtOH to give hydrated material.

Anal. Calcd. for C₂₇H₃₁NO₃.C₄H₆O₆.0.25 H₂O: C, 65.08; H, 6.61; N, 2.45. Found: 64.91; H, 6.71; N, 2.33.

The free base 20f was obtained in 70% yield and converted to the d-tartrate salt. Several recrystallizations from EtOH gave the hydroscopic salt, mp 144°-153° C.

Anal. Calcd. for C₂₉H₃₅NO₃.C₄H₆O₆.0.25 H₂O: C, 66.04; H, 6.97; N, 2.33. Found: C, 66.06; H, 7.02; N, 2.17.

J.
7β-Arylakyl-4,5α-epoxy-3-methoxy-6α,7α-(oxymethylene)-morphinans (22)

The N-cyano compounds were prepared by dropwise treatment of the free base 17 (1.0 equivalent) in CHCl₃ (1.0 g in 10 mL) containing finely powdered K₂CO₃ (1.5 equivalents) with a solution of cyanogen bromide (1.2 equivalents) in CHCl₃ (1.0 g in 20 mL). The mixture was stirred at room temperature for 30 min. and then refluxed for 2 hrs. The insoluble material was removed by filtration and the filtrate evaporated. The residue was azeotroped with EtOH until a foam formed. Compound 17c (16.6 g, 39.7 mmole) gave 16.3 g of 21c as a foam. This foam was dissolved in dioxane (500 mL) and KOH (465 mmole) in H₂O (100 mL) added. The mixture was refluxed 1 week, cooled and evaporated to a small volume. The residue was partitioned between H₂O and CHCl₃. Processing of the organic phase gave 16.0 g of a foam which was chromatographed to give 12.2 g (76%) of 22c as a foam. Crystalline 22c, mp 101°-102° C., was obtained upon trituration with EtOH. Hydrolysis of 21d for 5 days followed by workup gave 22d in nearly quantitative yield as a glass which was not further purified but used directly in alkylation reactions. Chromatography gave a 91% yield of 21e which was hydrolyzed to 22e and purified by chromatography to give material suitable for further reactions.

K.
7β-Arylalkyl-17-(cycloalkylmethyl)-4,5α-epoxy-3-methoxy-6α,7α-(oxymethylene)-morphinans (23P,B)

A solution of 22 in DMF (1 g in 20 mL) containing NaHCO₃ (2.5 equivalents) and cycloalkylmethyl bromide (1.2 equivalents) was heated in an oil bath at 100° C. while under argon until the reaction was complete as indicated by TLC (3-20 h). The mixture was cooled and filtered to remove insolubles. The filtrate was evaporated using an oil pump and the residue dissolved in H₂O. This mixture was adjusted to pH 10-11 with NH₄OH and extracted with 3 portions of toluene. The organic phase was processed in the usual manner, the residue chromatographed and the product 23 crystallized as the free base or HCl salt.

Compound 23Pc was directly crystallized in 60% yield as the free base, mp 144°-146.5° C., from EtOAc.

Anal. Calcd. for C₃₀H₃₅NO₃: C, 78.74; H, 7.71; N, 3.06. Found: C, 78.99; H, 7.81; N, 3.06.

Compound 23Pd was obtained as a foam in 93% yield after chromatography and converted to the d-tartrate salt which was obtained in crystalline form, mp 152°-157° C., from aqueous EtOH.

Anal. Calcd. for C₃₁H₃₇NO₃.C₄H₆O₆: C, 67.62; 6.97, N, 2.25. Found: C, 68.00; H, 6.85; N, 2.05.

Direct crystallization of the d-tartrate salt of 23Pe gave a 99% yield of crystals, mp 110°-115° C., from EtOH.

Anal. Calcd. for C₃₂H₃₉NO₃.C₄H₆O₆: C, 68.01; H, 7.13; N, 2.20. Found: C, 67.62; H, 7.26; N, 2.06.

Compound 23Bc was crystallized directly in 99% yield as the d-tartrate salt. Recrystallization from EtOH gave pure material, mp 137°-146° C.

Anal. Calcd. for C₃₁H₃₇NO₃.C₄H₆O₆: C, 67.72; H, 6.82; N, 2.26. Found: C, 67.68; H, 6.80; N, 2.46.

The free base of 23Bd was chromatographed to give an 89% yield of the free base as a foam. The d-tartrate salt, mp 130°-144° C. was obtained in crystalline form from EtOH.

Anal. Calcd. for C₃₂H₃₉NO₃.C₄H₆O₆: C, 68.01; H, 7.13; N, 2.20. Found: C, 68.08; H, 6.95; N, 2.06.

The d-tartrate salt of 23Be was obtained in 99% yield and recrystallized from EtOH. The mp of 23Be.d-tartrate was 128°-134° C.

Anal. Calcd. for C₃₃H₄₁NO₃.C₄H₆O₆: C, 68.39; H, 7.29; N, 2.16. Found: C, 68.08; H, 6.95; N, 2.06.

7β-Arylalkyl-17-(cycloalkylmethyl)-4,5α-epoxy-3-hydroxy-6α,7α-(oxymethylene)-morphinans (24P,B)

A mixture of 23 (free base) and 48% HBr (1 g in 10-20 mL) was refluxed in a preheated oil bath for 15 min. The cooled solution was diluted with H₂O, made basic with NH₄OH, and the 6α-hydroxy-7β-bromomethyl intermediate extracted with CHCl₃ or EtOAc. After processing of the organic phase and evaporation, the residue was dissolved in dioxane (30 mL) and 1 N NaOH (10 mL) added. The mixture was heated at 60°-70° C. for 90 min., then evaporated to dryness. The residue was dissolved in H₂O and the pH adjusted to ca. 8 with HOAc. Extraction with CHCl₃ was followed by chromatography.

Compound 24Pc was obtained as a foam in 53% yield. Crystals, mp 188°-190° C. were obtained from EtOAc.

Anal. Calcd. for C₂₉H₃₃NO₃: C, 78.54; H, 7.42; N, 3.40. Found: C, 78.52; H, 7.50; N, 3.16.

Compound 24Pd was obtained in 43% yield after chromatography. A crystalline acid addition salt could not be obtained.

Anal. Calcd. for $C_{30}H_{35}NO_3$: C, 78.74; H, 7.71; N, 3.06. Found: C, 78.34; H, 7.65; N, 2.77.

The d-tartrate salt of 24Pe crystallized in 81% yield without prior chromatography. Recrystallization from EtOAc gave solvated material, foams 147°–170° C.

Anal. Calcd. for $C_{31}H_{37}NO_3 \cdot C_4H_6O_6 \cdot 0.5$ EtOAc: C, 66.75; H, 7.12; N, 2.10. Found: C, 66.70; H, 7.21; N, 2.11.

Compound 24Bc was obtained in 42% yield after chromatography. The free base, mp 200°–202° C. crystallized from EtOAc.

Anal. Calcd. for $C_{30}H_{35}NO_3$: C, 78.74; H, 7.71; N, 3.06. Found: C, 78.43; H, 7.79; N, 2.95.

Compound 24Bd was obtained in 62% yield after chromatography. The d-tartrate salt, mp 160°–176° C., crystallized from EtOAc.

Anal. Calcd. for $C_{31}H_{37}NO_3 \cdot C_4H_6O_6$: C, 67.62; H, 6.97; N, 2.25. Found: C, 67.52; H, 6.75; N, 1.88.

The free base of 24Be was obtained in 82% yield and was obtained as crystals, mp 158°–159° C., from EtOH.

Anal. Calcd. for $C_{32}H_{29}NO_3$: C, 79.14; H, 8.09; N, 2.88. Found: C, 79.16; H, 8.02; N, 2.88.

EXAMPLE III

Acetic Acid Induced Mouse Writhing Test

Analgesic effects of the test compounds were determined in mice by use of the acetic acid induced writhing test described by B. A. Whittle, *Brit. J. Pharmacol.*, 22:246 (1964). In this test, at least 3 groups of 5 male CD-1 mice each were given subcutaneous doses of the test drug dissolved in distilled water. In all cases, 0.4 mL of a 0.5% v/v acetic acid in distilled water solution was administered intraperitoneally 15 min. post drug. The number of writhes in a 20 min. interval beginning 5 min. after the acetic acid injection were determined and compared with the number of writhes in a control group which had received only acetic acid.

Percent inhibition of writhing was calculated as:

$$\% \text{ inhibition} = \frac{\text{No. Control Writhes} - \text{No. Treated Writhes}}{\text{No. Control Writhes}}$$

The $ED_{50}$ dose, i.e., the dose required to reduce the number of writhes by 50%, was determined graphically from a plot of % inhibition as a probit verus log dose. Confidence limits of 95% were calculated on the basis of those results falling in the range 16–84% inhibition. See Lichtfield, J. T. and Wilcoxon, F., *J. Pharmacol. Exp. Ther.*, 96, 99–113 (1949).

The results of this testing, both in terms of μ mole/kg and mg/kg of the compound tested, are set out in table I.

TABLE I

Analgesic Activity In Mouse Writhing Assay - Subcutaneous Inj.

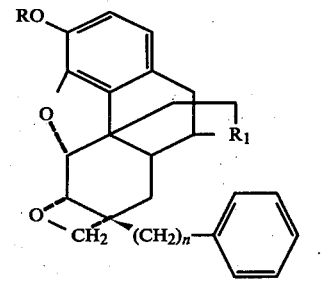

| Compound | R | $R_1$ | n | $ED_{50}$ (μmole/kg) | $ED_{50}$ (mg/kg) |
|---|---|---|---|---|---|
| 17c* | $CH_3$ | $CH_3$ | 2 | 0.90 | 0.50 |
| 17d* | $CH_3$ | $CH_3$ | 3 | 0.046 | 0.027 |
| 17e* | $CH_3$ | $CH_3$ | 4 | 0.005 | 0.0028 |
| 17f* | $CH_3$ | $CH_3$ | 5 | 1.3 | 0.82 |
| 20c* | H | $CH_3$ | 2 | 0.048 | 0.024 |
| 20d* | H | $CH_3$ | 3 | 0.019 | 0.011 |
| 20e* | H | $CH_3$ | 4 | 0.024 | 0.014 |
| 20f* | H | $CH_3$ | 5 | 0.028 | 0.017 |
| 23Pc | $CH_3$ | CPM | 2 | 0.57 | 0.26 |
| 23Pd* | $CH_3$ | CPM | 3 | 1.07 | 0.67 |
| 23Pe* | $CH_3$ | CPM | 4 | 0.61 | 0.39 |
| 23Bc* | $CH_3$ | CBM | 2 | >16 | >10 |
| 23Bd* | $CH_3$ | CBM | 3 | 4.4 | 2.8 |
| 23Be* | $CH_3$ | CBM | 4 | 2.8 | 1.8 |
| 24Pc | H | CPM | 2 | 0.04 | 0.018 |
| 24Pd | H | CPM | 3 | 0.003 | 0.0015 |
| 24Pe* | H | CPM | 4 | 0.015 | 0.01 |
| 24Bc | H | CBM | 2 | 0.39 | 0.177 |
| 24Bd* | H | CBM | 3 | 0.06 | 0.0375 |
| 24Be | H | CBM | 4 | 0.05 | 0.22 |

*= d-tartrate salt
$R_1$ = CPM = cyclopropylmethyl;
CBM = cyclobutylmethyl

The compounds claimed herein, especially those with small $ED_{50}$ values, are very potent narcotic agonists. As such, they are useful for the relief of pain, for pre-operative anesthesia or for the immobilization of large animals. The dose to be administered to achieve the desired result, i.e., the effective dose, may vary from individual to individual but is readily determined by one skilled in the art without undue experimentation.

The compounds of the present invention form pharmacologically active addition salts with organic acids. Typical acid addition salts are the tartrate and maleate. These compounds may be administered by known conventional methods such as intravenous, parenteral, buccal, rectal or oral routes. Dose forms for the administration of these compounds can be prepared by methods recognized in the pharmaceutical sciences.

What is claimed is:

1. 7β-arylalkyl-6α,7α-oxymethylene-3-methoxy or 3-hydroxy-4,5α-epoxy-17-methyl or 17-cycloalkylmethyl-morphinans characterized by the formula:

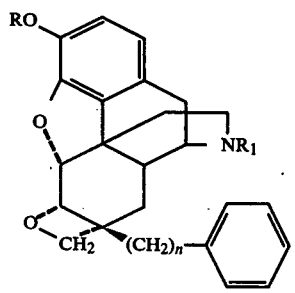

wherein R is H or methyl, R₁ is methyl, cyclopropylmethyl or cyclobutylmethyl and n is 2 to 5.

2. A compound as characterized by claim 1 wherein R is methyl, R₁ is methyl and n is 2.

3. A compound as characterized by claim 1 wherein R is methyl, R₁ is methyl and n is 3.

4. A compound as characterized by claim 1 wherein R is methyl, R₁ is methyl and n is 4.

5. A compound as characterized by claim 1 wherein R is methyl, R₁ is methyl and n is 5.

6. A compound as characterized by claim 1 wherein R is H, R₁ is methyl and n is 2.

7. A compound as characterized by claim 1 wherein R is H, R₁ is methyl and n is 3.

8. A compound as characterized by claim 1 wherein R is H, R₁ is methyl an n is 4.

9. A compound as characterized by claim 1 wherein R is H, R₁ is methyl and n is 5.

10. A compound as characterized by claim 1 wherein R is methyl, R₁ is cyclopropylmethyl and n is 2.

11. A compound as characterized by claim 1 wherein R is methyl, R₁ is cyclopropylmethyl and n is 3.

12. A compound as characterized by claim 1 wherein R is methyl, R₁ is cyclopropylmethyl and n is 4.

13. A compound as characterized by claim 1 wherein R is methyl, R₁ is cyclobutylmethyl and n is 3.

14. A compound as characterized by claim 1 wherein R is methyl, R₁ is cyclobutylmethyl and n is 4.

15. A compound as characterized by claim 1 wherein R is H, R₁ is cyclopropylmethyl and n is 2.

16. A compound as characterized by claim 1 wherein R is H, R₁ is cyclopropylmethyl and n is 3.

17. A compound as characterized by claim 1 wherein R is H, R₁ is cyclopropylmethyl and n is 4.

18. A compound as characterized by claim 1 wherein R is H, R₁ is cyclobutylmethyl and n is 2.

19. A compound as characterized by claim 1 wherein R is H, R₁ is cyclobutylmethyl and n is 3.

20. A compound as characterized by claim 1 wherein R is H, R₁ is cyclobutylmethyl and n is 4.

* * * * *